US010549218B2

(12) United States Patent
Olivier et al.

(10) Patent No.: US 10,549,218 B2
(45) Date of Patent: Feb. 4, 2020

(54) METHOD AND APPARATUS FOR FILTERING A LIQUID SAMPLE

(75) Inventors: Stephane Olivier, Rosheim (FR); Didier Metz, Stotzheim (FR)

(73) Assignee: EMD Millipore Corporation, Burlington, MA (US)

( * ) Notice: Subject to any disclaimer, the term of this patent is extended or adjusted under 35 U.S.C. 154(b) by 528 days.

(21) Appl. No.: 14/119,496

(22) PCT Filed: Jun. 8, 2012

(86) PCT No.: PCT/US2012/041568
§ 371 (c)(1),
(2), (4) Date: Feb. 10, 2014

(87) PCT Pub. No.: WO2013/106081
PCT Pub. Date: Jul. 18, 2013

(65) Prior Publication Data
US 2014/0202967 A1    Jul. 24, 2014

(30) Foreign Application Priority Data

Jun. 27, 2011   (EP) .................................... 11290290

(51) Int. Cl.
*B01D 27/04*  (2006.01)
*G01N 1/40*   (2006.01)

(52) U.S. Cl.
CPC ........... *B01D 27/04* (2013.01); *G01N 1/4077* (2013.01); *G01N 2001/4088* (2013.01)

(58) Field of Classification Search
None
See application file for complete search history.

(56) References Cited

U.S. PATENT DOCUMENTS 2,449,238 A * 9/1948 Lightfoot, Jr. ......... B01D 23/28
                                                        100/106
3,041,669 A   7/1962 Marshall et al.
(Continued)

FOREIGN PATENT DOCUMENTS

CN       1672765 A    9/2005
CN    101687351 A    3/2010
(Continued)

OTHER PUBLICATIONS

Extended Supplemental European Search Report received for European Patent Application No. 12864824.3, dated Dec. 11, 2014, 9 pages.
(Continued)

*Primary Examiner* — Kara M Peo
(74) *Attorney, Agent, or Firm* — Nields, Lemack & Frame, LLC

(57) ABSTRACT

The invention relates to the filtering of liquid samples, preferably in a laboratory environment, for example for collecting micro organisms from the liquid sample for subsequent testing. The invention provides a method for filtering a liquid sample which comprises providing a blank of a deformable sheet material and a filtration medium, deforming the blank to form a funnel extending above and about the filtration medium, introducing the liquid sample to be filtered into the so formed funnel, and filtering the liquid sample from the funnel through the filtration medium, for example to a downstream receptacle. The method is accordingly based on the concept that the funnel is not or at least not completely preformed but provided in a form of a blank of a deformable material sheet which is deformed so as to form the funnel at the point and time of use during filtration.

12 Claims, 13 Drawing Sheets

(56) References Cited

U.S. PATENT DOCUMENTS

Figure 1A:
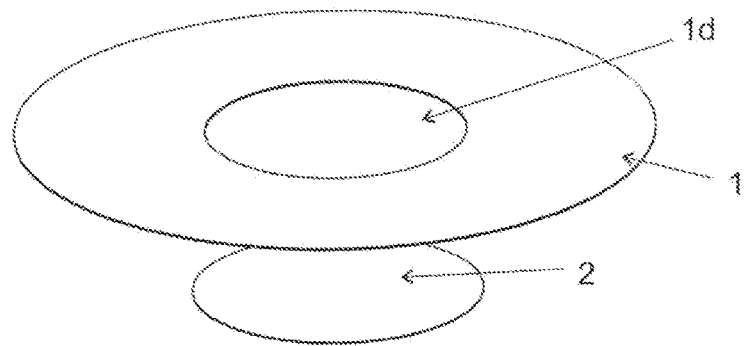

| | | | |
|---|---|---|---|
| 3,252,403 A | 5/1966 | Polizzi |
| 3,608,055 A | 9/1971 | Long |
| 3,615,257 A | 10/1971 | Frost et al. |
| 3,838,978 A | 10/1974 | Eddleman et al. |
| 3,971,305 A | 7/1976 | Daswick |
| 4,123,215 A | 10/1978 | Madenokoji |
| 4,301,010 A | 11/1981 | Eddleman et al. |
| 4,317,726 A | 3/1982 | Shepel |
| 4,533,472 A | 8/1985 | Verri et al. |
| 4,895,706 A | 1/1990 | Root et al. |
| 5,112,488 A | 5/1992 | Lemonnier |
| 5,234,585 A | 8/1993 | Zuk, Jr. |
| 5,343,909 A | 9/1994 | Goodman |
| 5,421,997 A | 6/1995 | Gerteis |
| 5,695,639 A | 12/1997 | Johnson |
| 5,792,356 A | 8/1998 | Yuan |
| 5,868,928 A | 2/1999 | Bradley |
| 6,358,730 B1 | 3/2002 | Kane |
| 6,443,314 B2 | 9/2002 | Shiraiwa et al. |
| 6,750,039 B1 | 6/2004 | Bargoot et al. |
| 6,921,480 B2 | 7/2005 | Post |
| 7,025,923 B2 | 4/2006 | Harhen et al. |
| 7,661,538 B1 | 2/2010 | Zuk, Jr. |
| 2001/0032821 A1 | 10/2001 | Drocourt et al. |
| 2001/0052491 A1 | 12/2001 | Shiraiwa et al. |
| 2003/0057148 A1 | 3/2003 | Zuk |
| 2004/0065622 A1 | 4/2004 | Ferguson |
| 2004/0222147 A1 | 11/2004 | Post |
| 2007/0144959 A1 | 6/2007 | Zuk, Jr. |
| 2008/0097240 A1 | 4/2008 | Rebec et al. |

FOREIGN PATENT DOCUMENTS

| | | |
|---|---|---|
| EP | 0456252 A2 | 11/1991 |
| EP | 0881930 A1 | 12/1998 |
| GB | 2209127 A | 5/1989 |
| JP | 7-313812 A | 12/1995 |
| JP | 8-266816 A | 10/1996 |
| WO | 1988/006723 A1 | 9/1988 |
| WO | 1994/005395 A1 | 3/1994 |
| WO | 1997/027925 A1 | 8/1997 |
| WO | 2007/038478 A2 | 4/2007 |
| WO | 2008/113444 A1 | 9/2008 |
| WO | 2010/078891 A1 | 7/2010 |

OTHER PUBLICATIONS

International Preliminary Report on Patentability received for PCT Patent Application No. PCT/US2012/041568, dated Jan. 9, 2014, 10 pages.

International Search Report and Written Opinion received for PCT Patent Application No. PCT/US2012/041568, dated Aug. 8, 2013, 12 pages.

Indian communication, dated Mar. 21, 2018 in corresponding Indian patent application No. 9359/DELNP/2013.

* cited by examiner

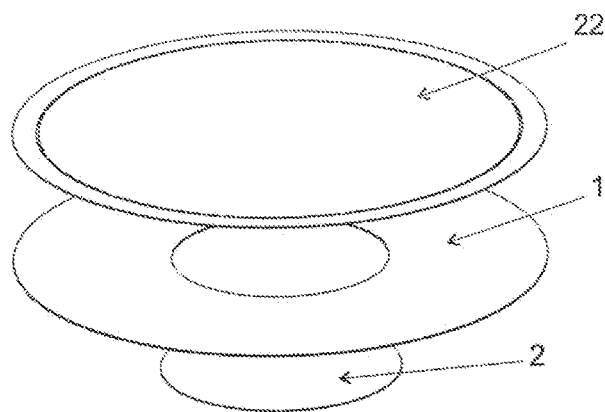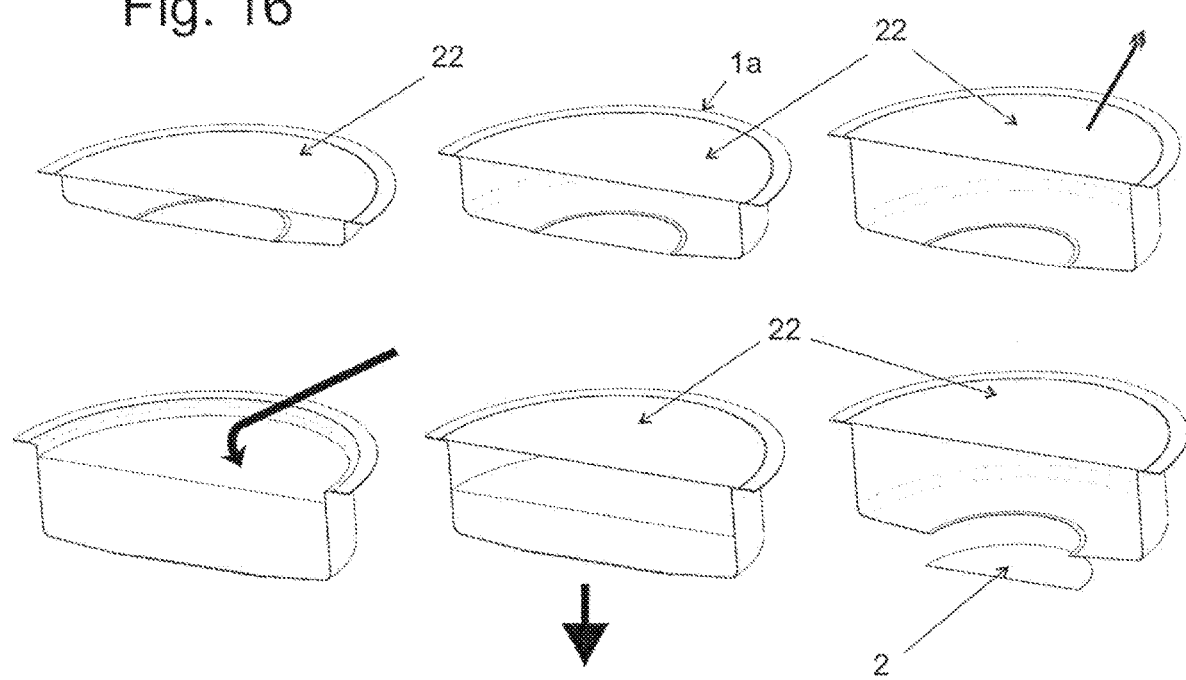

METHOD AND APPARATUS FOR FILTERING A LIQUID SAMPLE

CROSS-REFERENCED TO RELATED APPLICATIONS

The present application is a U.S. National Stage Application of International Application No. PCT/US2012/041568, filing date Jun. 8, 2012, which claims the benefit of priority of European Patent Application No. 11290290.3, filing date Jun. 27, 2011, each of which is incorporated by reference herein in its entirety.

The present invention relates to the filtering of liquid samples, preferably in a laboratory environment, for example for collecting micro organisms from the liquid sample for subsequent testing.

Devices for filtering liquid samples and methods employing such devices mainly rely on a vacuum filter apparatus which comprises generally an upper reservoir member for receiving the liquid sample, a support for a filtration membrane at a bottom of the upper reservoir member, and a lower reservoir member for receiving and holding the liquid having passed the filtration membrane. The upper and lower reservoir members can be separated from each other so as to gain access to the filtration membrane carrying the micro organisms. The membrane is then manually transferred with the filtered micro organisms on it, preferably by the use of tweezers, to other processing equipment or stages, i.e. a Petri dish or a pad impregnated with liquid media.

Vacuum filtration devices for this purpose exist in a number of concepts. Some of them are for multiple use so that cleaning and sterilization is required between the processing of different batches of liquid samples. Others being disposable or one-way devices which are discarded after the use. Other higher sterility standards require individual sterile packaging which directly impacts the overall product size.

There is a recent trend in the pharmaceutical and food and beverage industries that volumes of liquid samples to be filtered in such devices increase to volumes of 100 ml or more and there is a simultaneous trend towards an increased sustainability which forces these industries to reduce the amount of resources used and the size and weight of waste produced by such processes because storage, shipment and waste processing incurs increased costs and environmental impact. Even for multi-use equipment the waste incurred by sterilization and cleaning leaves a negative environmental foot-print due to the necessity to produce, treat, process and dispose of the sterilizing and cleaning agents and to consume energy.

A multiple-use example of a filter device or funnel commonly used in chemical or other laboratories for the vacuum filtration of liquids, wherein the filter is to be readily removable after a filtration, is described in WO 97/27925. This vacuum filter funnel consists of two pieces, i.e. an upper reservoir member and a lower spout member which are removably combined for the filtration process. A filter disk rests on an integral grid at a top of the lower spout member and is held in place between the upper and lower members by solely the weight of the upper member. The filter disk is readily removed after simply lifting up the upper reservoir member. Both the reservoir and spout members are preferably constructed of a chemical and heat-resistant organic plastic so that the parts may be sterilized in an autoclave.

U.S. Pat. No. 4,301,010 discloses another vacuum filter funnel useful for separating solids from liquids which comprises a funnel with a lower spout which protrudes through a bottom outlet of a vacuum intake member. An upper funnel member has a perforated bottom plate on which a filter medium is removably positioned and held in place on the support by a threaded sleeve screwed into the upper funnel member until its lower surface abuts the filter medium at the periphery and holds it tightly against the perforated plate. This apparatus also is a re-usable device.

U.S. Pat. No. 3,838,978 discloses a further apparatus for performing laboratory vacuum filtration with a removable filter element. The device comprises a glass funnel which has a cylindrically shaped upper wall, a frustoconical intermediate section and a hollow cylindrical stem. A porous disk is provided for removably holding a filter paper over an upper surface of the disk by an O-ring seated in a peripheral groove formed in the peripheral side of the disk. The assembly of the porous disk, the piece of filter paper and the elastomeric O-ring is inserted into the cylindrically shaped upper wall of the glass funnel.

U.S. Pat. No. 7,661,538 B1 discloses a disposable vacuum filtration funnel usable for filtering fluids. The filtration funnel contains a cup-shaped rigid element with a peripheral wall and a filter on a drain structure at the bottom portion. The filter, for example a micro porous filter, is sealed to a filter seal surface on the bottom portion with a heat seal, an ultrasonic seal, a solvent seal, a glue seal or any other type of liquid-tight seal. The filter support supports the filter and places the downstream side of the filter in fluid flow communication with an outlet of the vacuum filtration funnel. A further pre-filter can be removably inserted into the cylindrical upper part and held therein by means of a seal ring which is press-fitted into the funnel so that an outer surface of the seal ring presses against an inner wall of the vacuum filtration funnel and a bottom surface of the seal ring presses against the top surface of the outer periphery of the pre-filter to seal the pre-filter to the vacuum filtration funnel.

None of these devices are suitable to cope with the apparent demands of sustainability.

It is an object of the present invention to provide a method of filtering a liquid sample and an apparatus for filtering a liquid sample which meets these requirements.

To solve this problem the present invention provides a method for filtering a liquid sample and an apparatus for filtering a liquid sample as well as a blank for use in the method or in combination with the apparatus. Preferred embodiments of the method, of the apparatus and of the blank are defined herein.

The present invention provides a method for filtering a liquid sample which comprises providing a blank of a deformable sheet material and a filtration medium, deforming the blank to form a funnel extending above and about the filtration medium, introducing the liquid sample to be filtered into the so formed funnel, and filtering the liquid sample from the funnel through the filtration medium, for example to a downstream receptacle.

The present invention is accordingly based on the concept that the funnel is not or at least not completely preformed but provided in a form of a blank of a deformable material sheet which is deformed so as to form the funnel at the point and time of use during filtration.

The apparatus for performing such a filtering method comprises a bowl defining a cavity, a first holder for holding a peripheral portion of a blank of sheet material and a piston located in the cavity and including a support for the filtration medium. The support communicates with a drain for the liquid, i.e. a downstream receptacle, and the piston includes the second holder for holding a more central portion of the blank of the sheet material about this support. In order to deform the blank to form a funnel, the bowl and the piston are movable relative to each other such that the blank of sheet material held at the first and second holders is deformed at the point and time of use within the cavity to extend above and about the filtration membrane on the support.

The remarkable advantages of the concept of the present invention are that the blank of the deformable material sheet provided to form the funnel can be stored, before use, in a flat form and requires only a minimum storage volume even if stored in large quantities. Furthermore, the amount of material used to form the blank can be very small so that the environmental impact is considerably reduced as compared to existing filtration concepts based on a rigid funnel structure. Since the material sheet more or less returns to its original flat form after use, the volume of the waste is considerably reduced as well as compared to existing structures.

In the method and the apparatus the funnel can be expanded in the bowl to the required filtration volume with the aid of the piston and, preferably, by the application of vacuum. After the filtration of the sample liquid, which can be effectuated by the aid of vacuum as well, the funnel can be discarded and the filter membrane can be removed and subjected to further analysis, i.e. microbial testing.

The concept of the invention additionally provides considerable flexibility as regards to the volume of the funnel since the deformation can be effected in a scaled manner. This could either save costs if varying volumes are required but identical blanks are used so that the number of varieties of blanks is reduced, or it could save time if identical blanks are deformed less if smaller volumes are sufficient. Alternatively, considerably different sample volumes can be dealt with using the same apparatus or equipment if different blanks are provided that are suitable to be deformed into funnels of different volume.

The present invention will now be described by way of example referring to preferred embodiments of an apparatus for filtering the liquid sample which is shown in the attached drawing. Variations of the method and the apparatus are of course possible and are described in connection with the various features where the modifications could be made.

SHORT DESCRIPTION OF THE DRAWING

Figure 2:
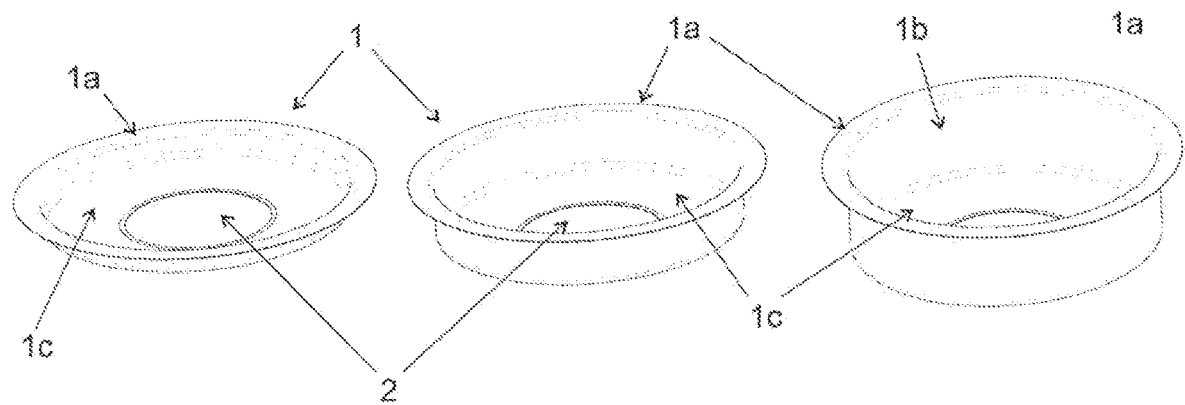
Figure 3A:
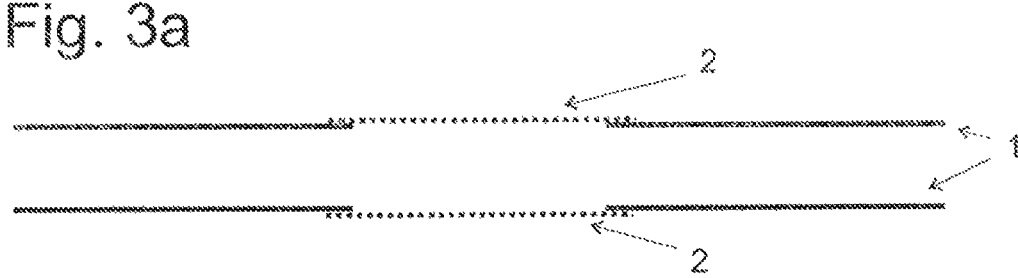
Figure 4A:
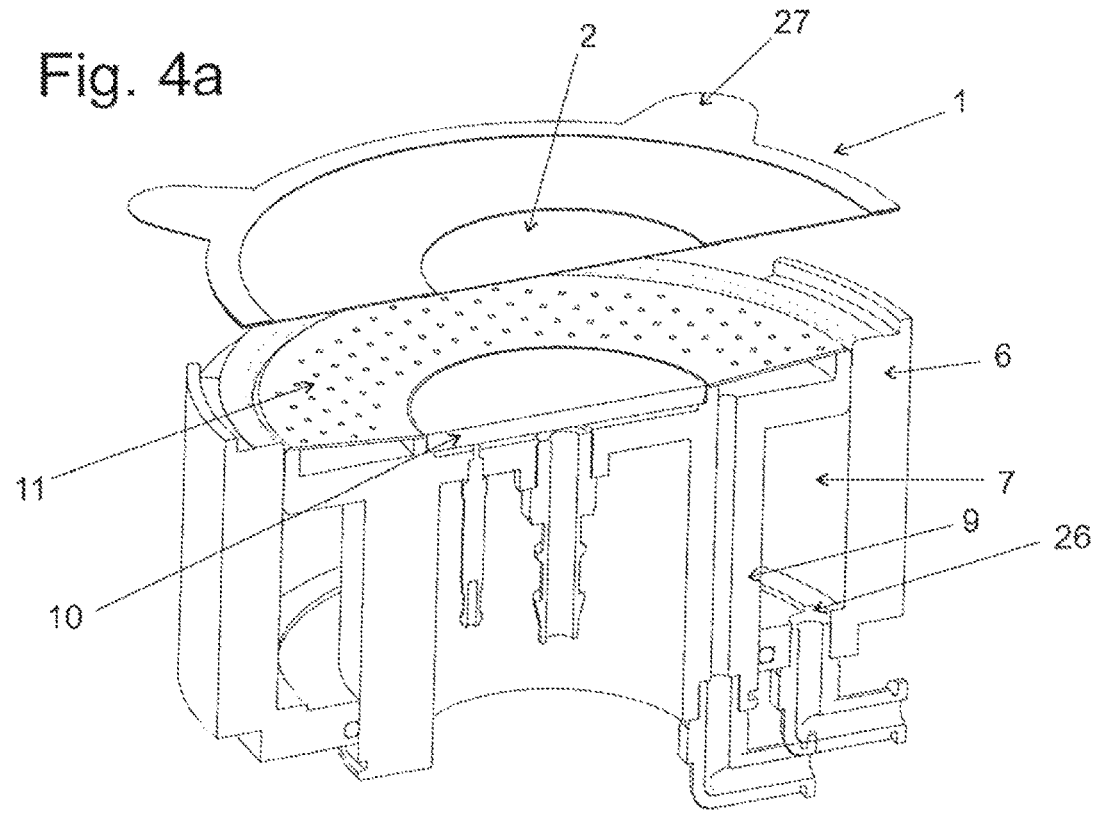
Figure 4B:
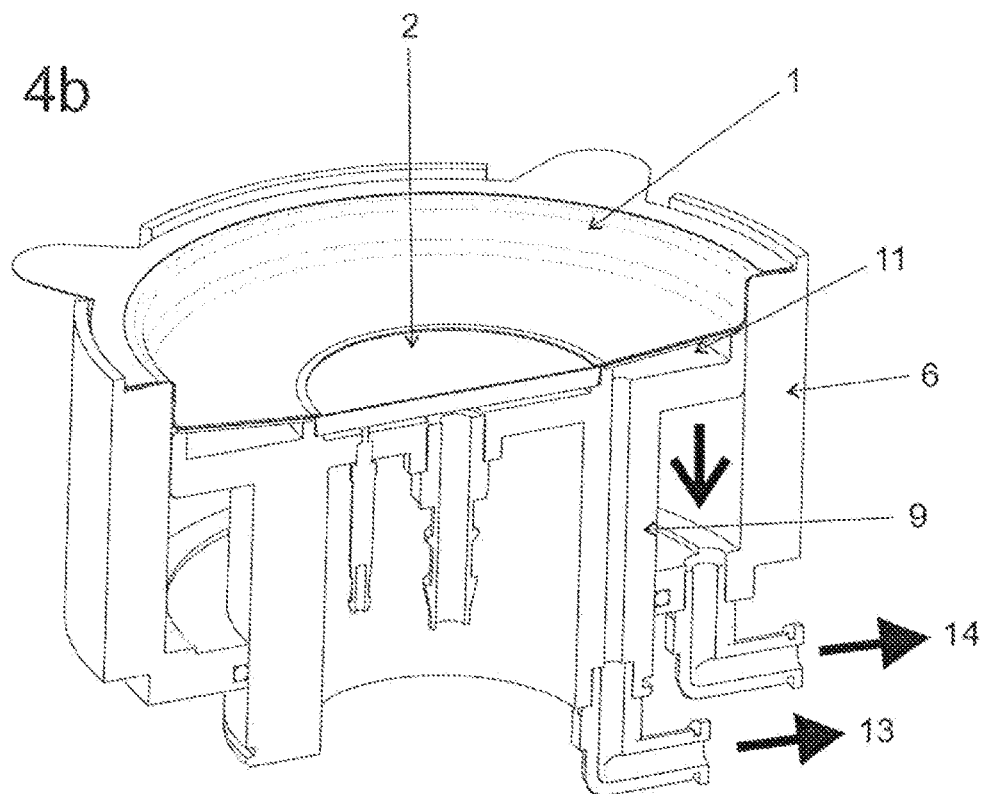
Figure 5A:
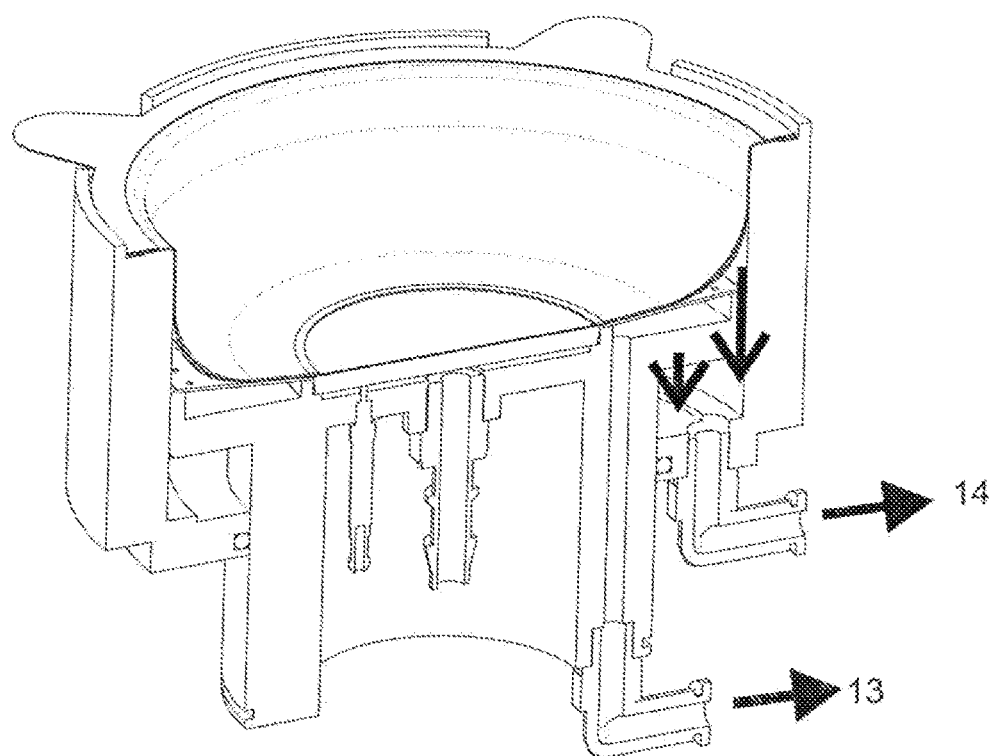
Figure 5B:
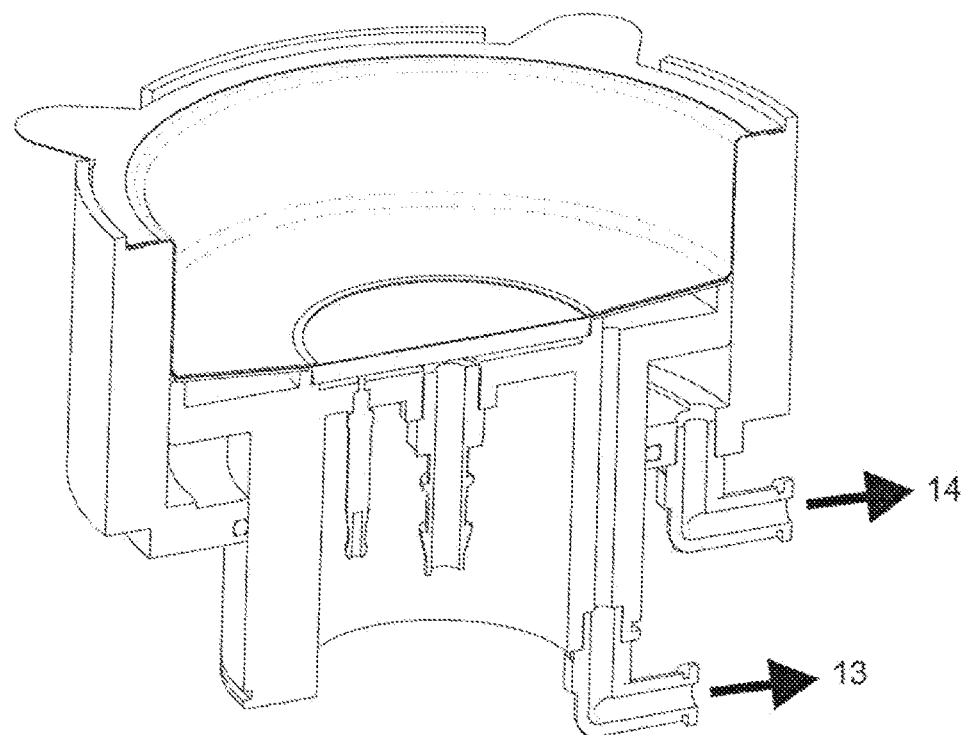
Figure 6:
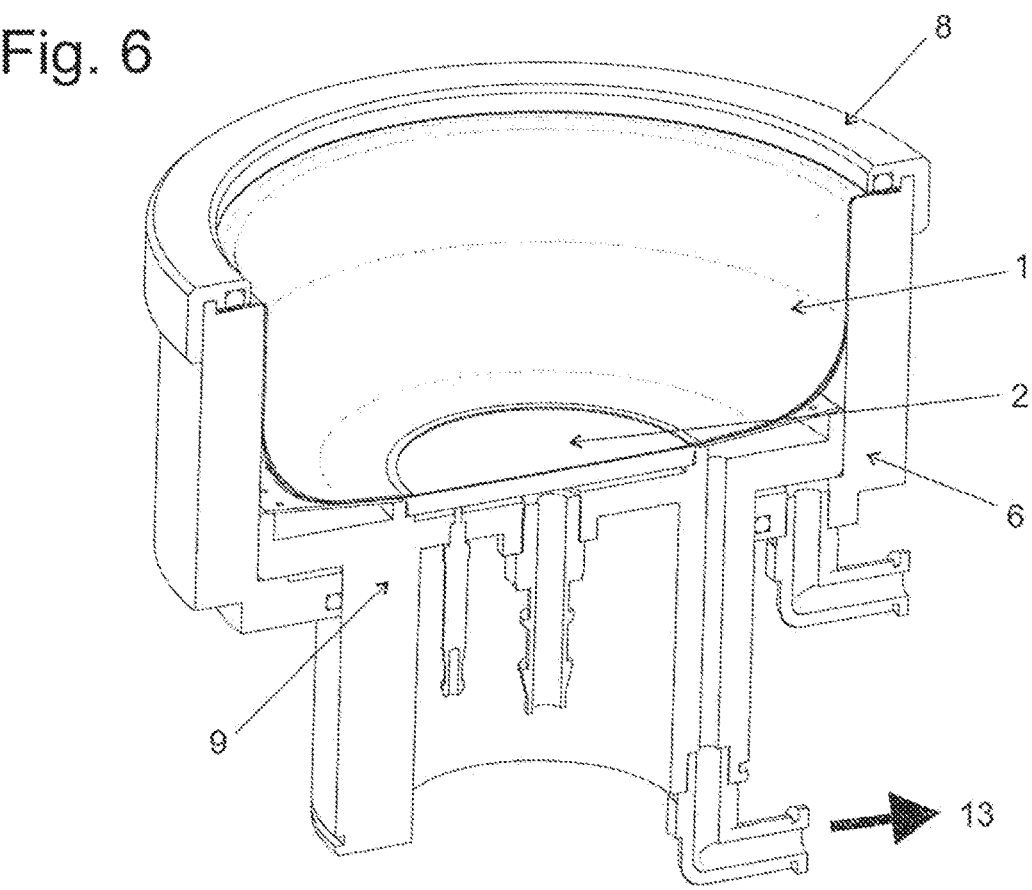
Figure 7:
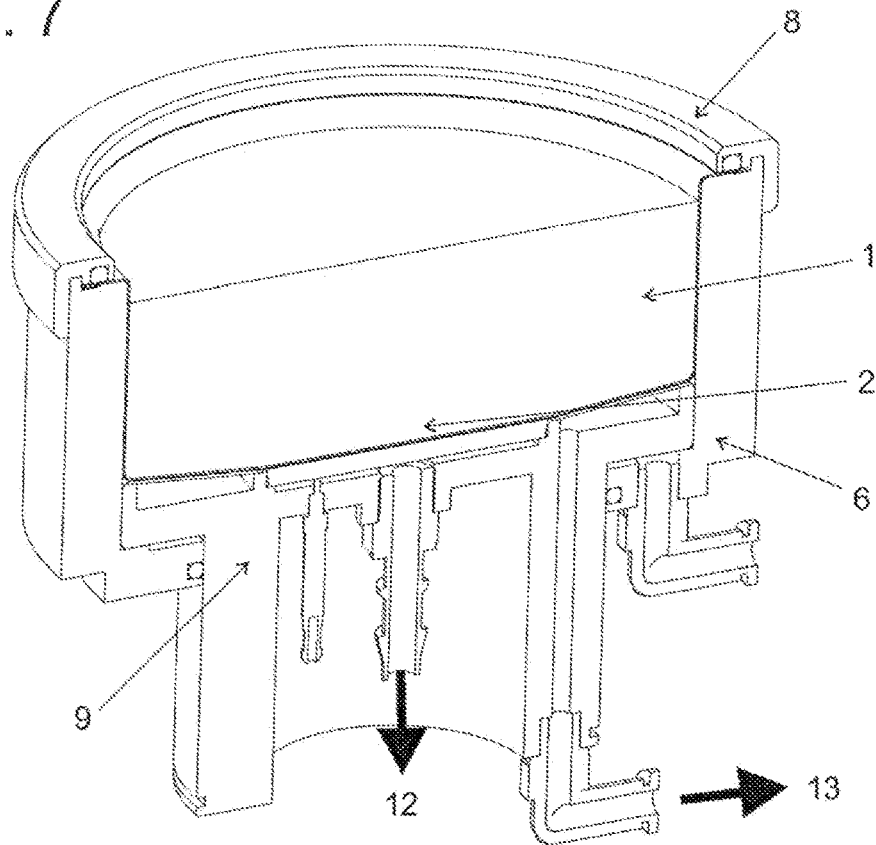
Figure 8:
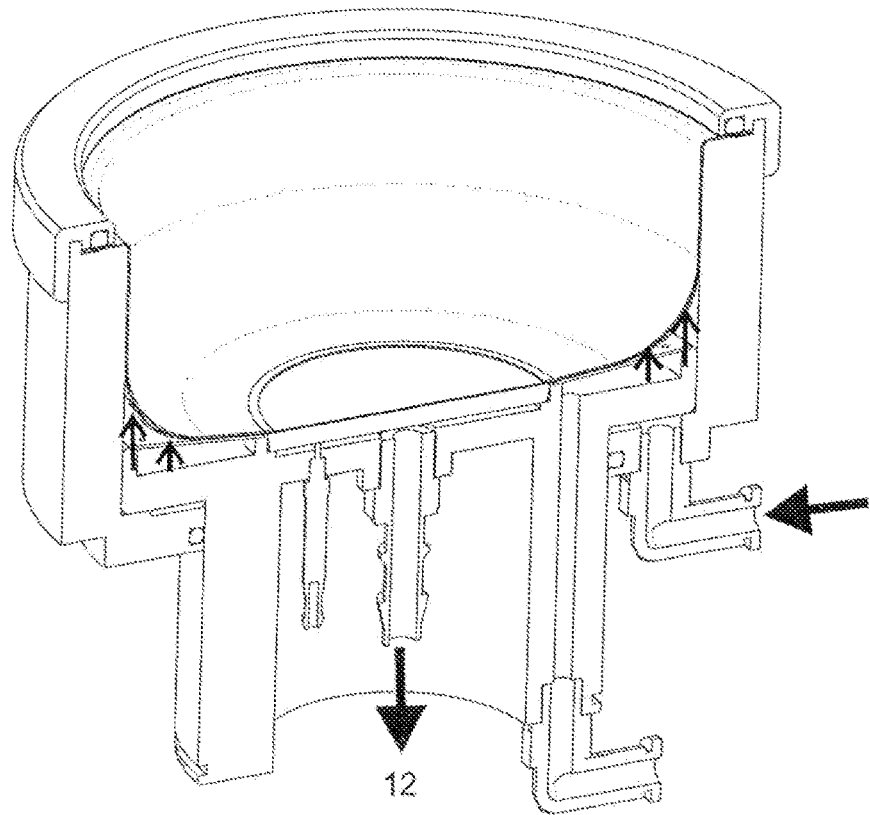
Figure 9:
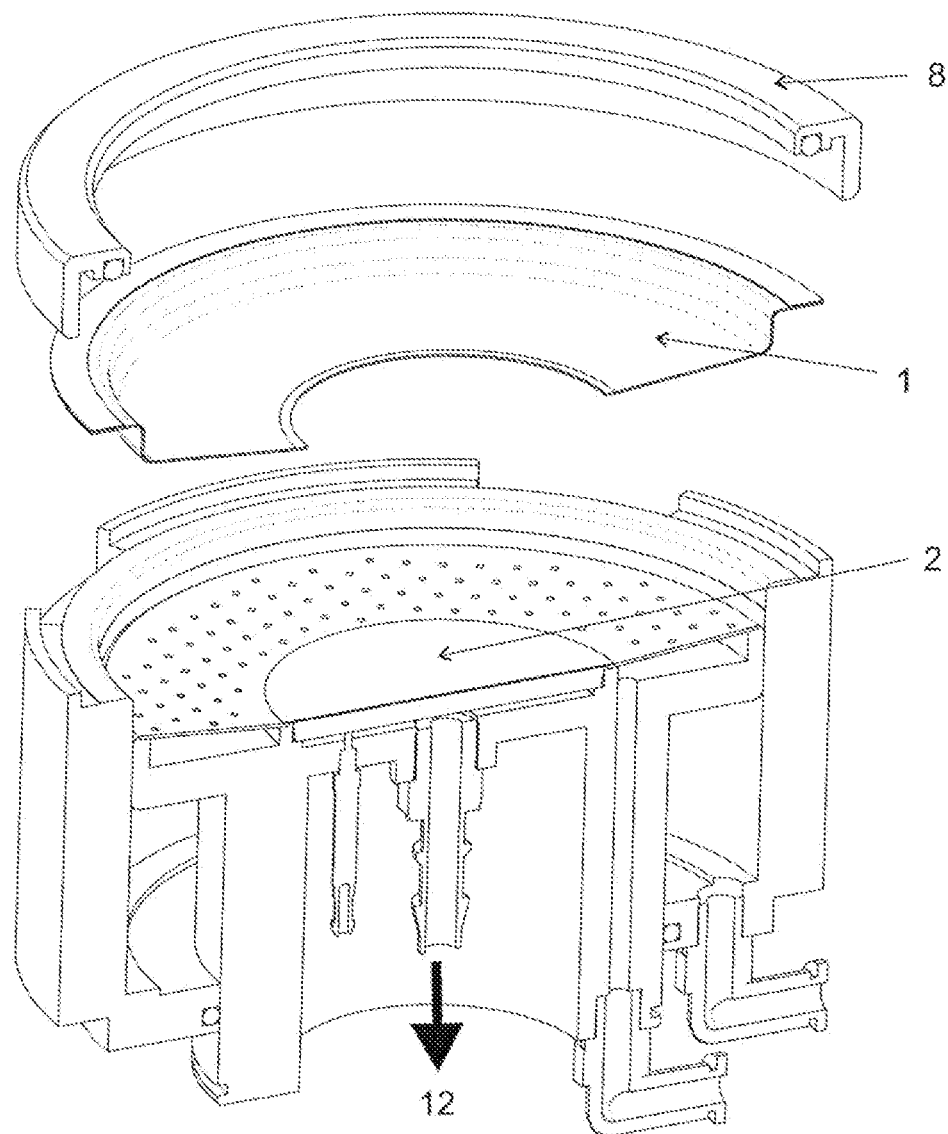
Figure 10:
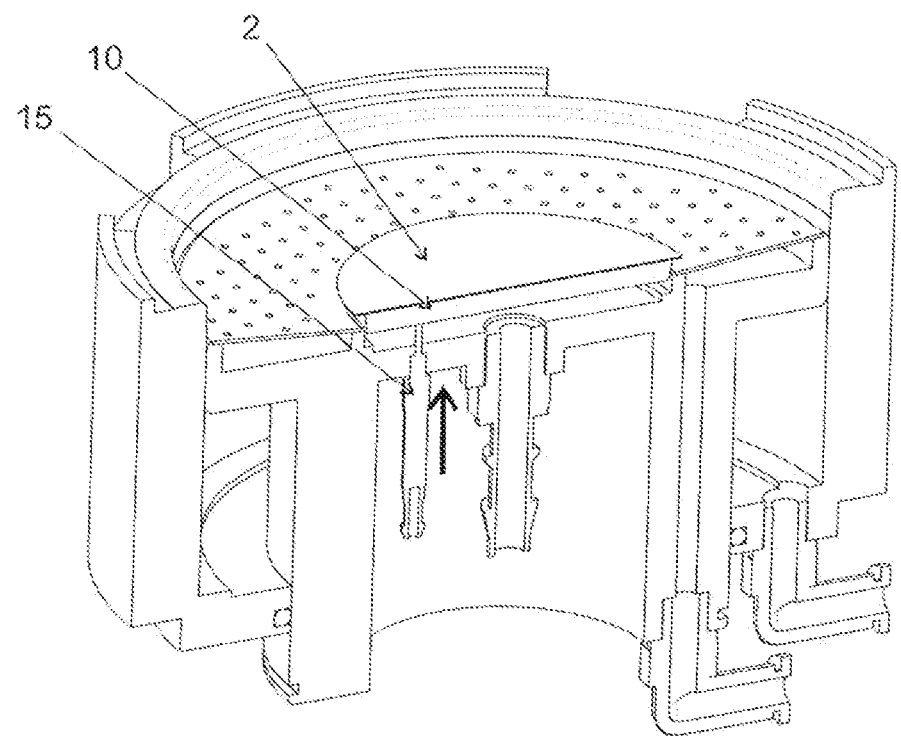
Figure 11:
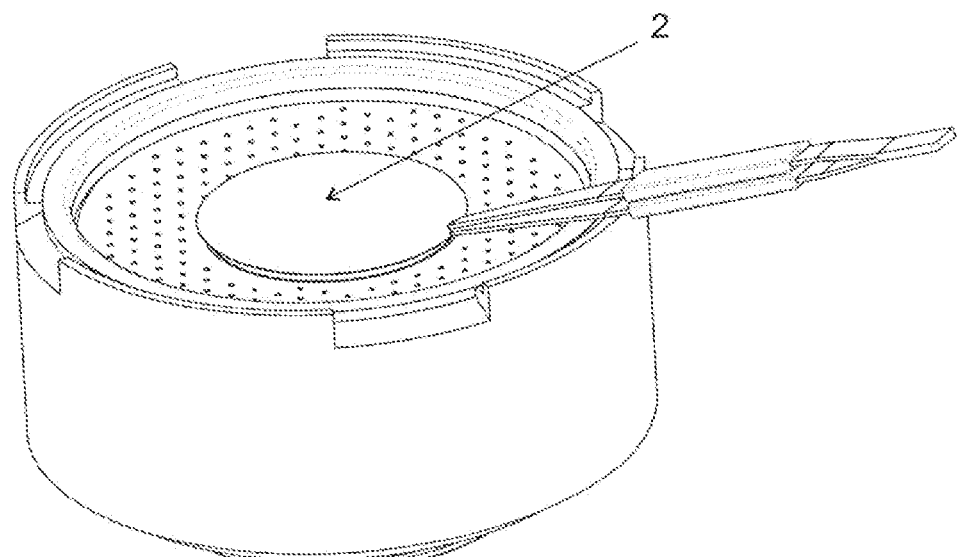
Figure 12:
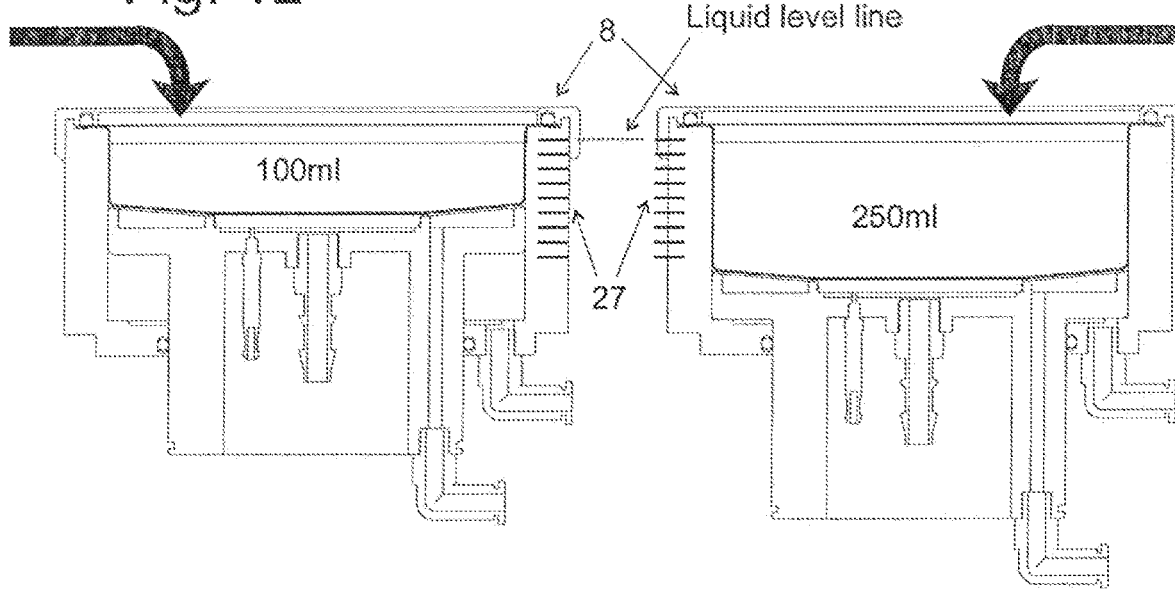
Figure 13:
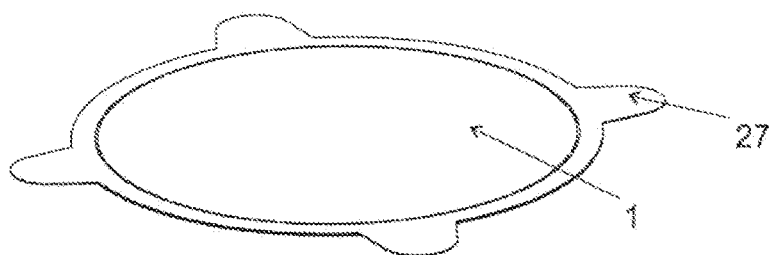
Figure 14:
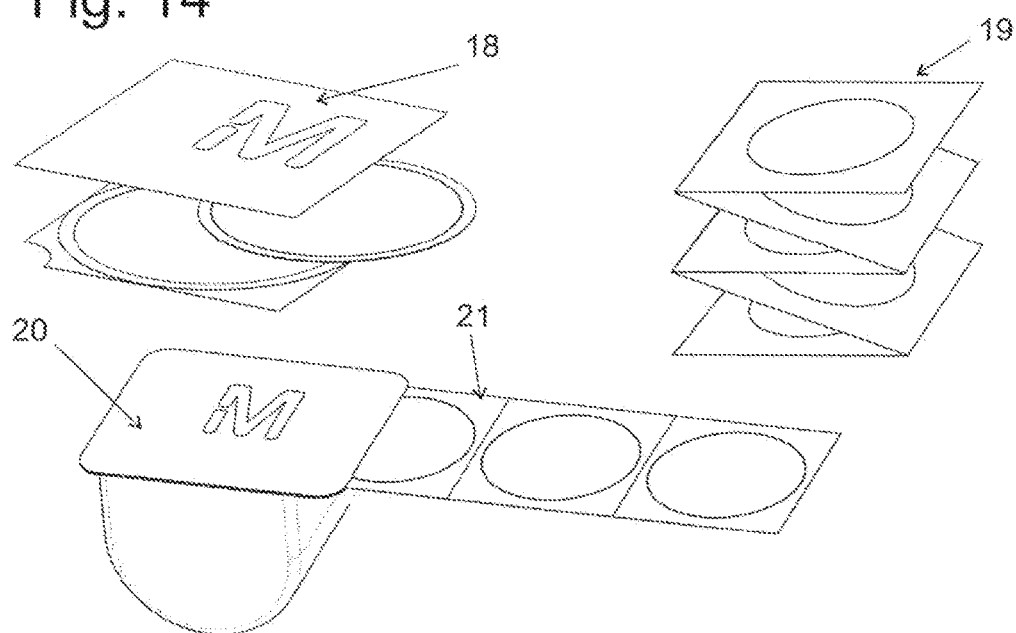
Figure 17:
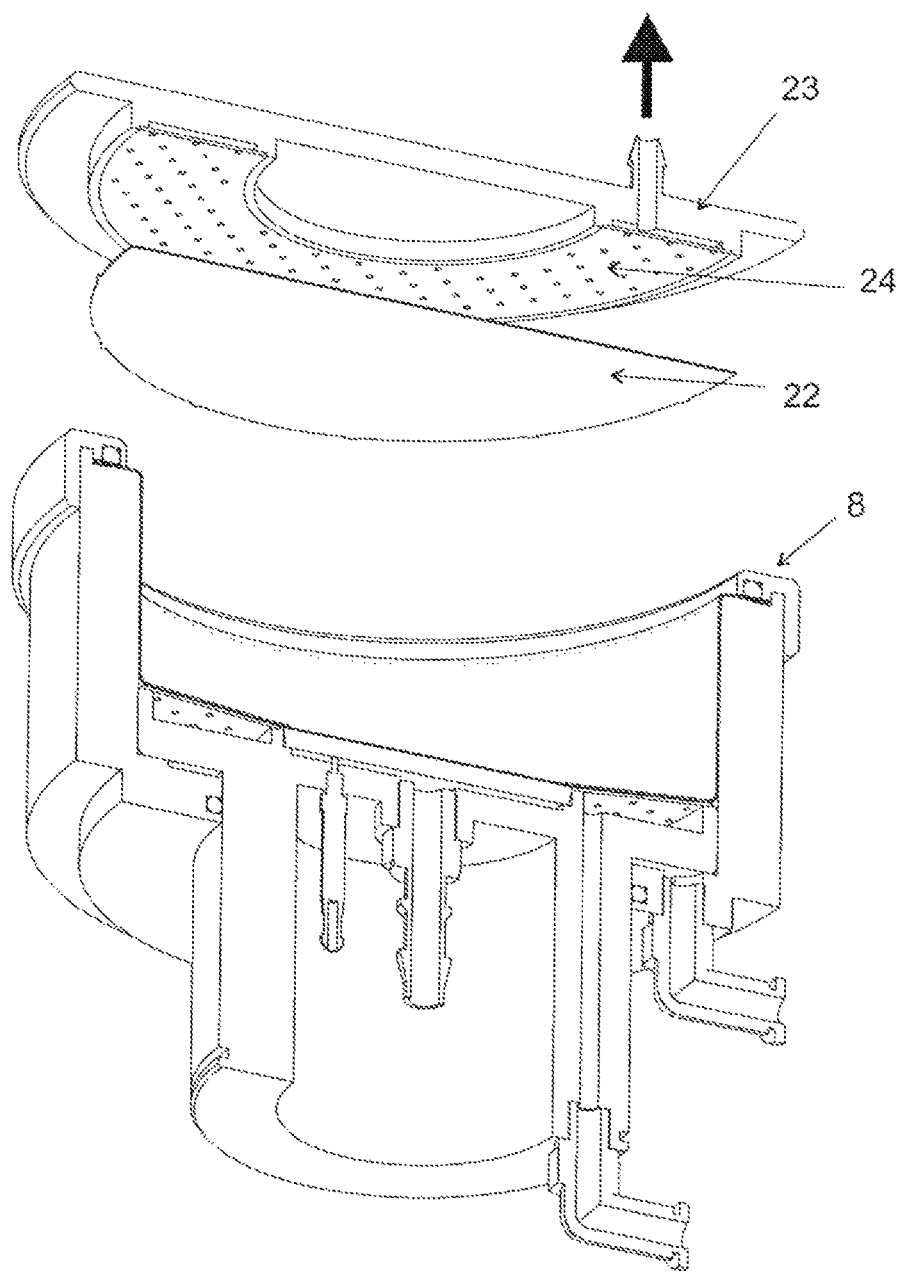
Figure 18:
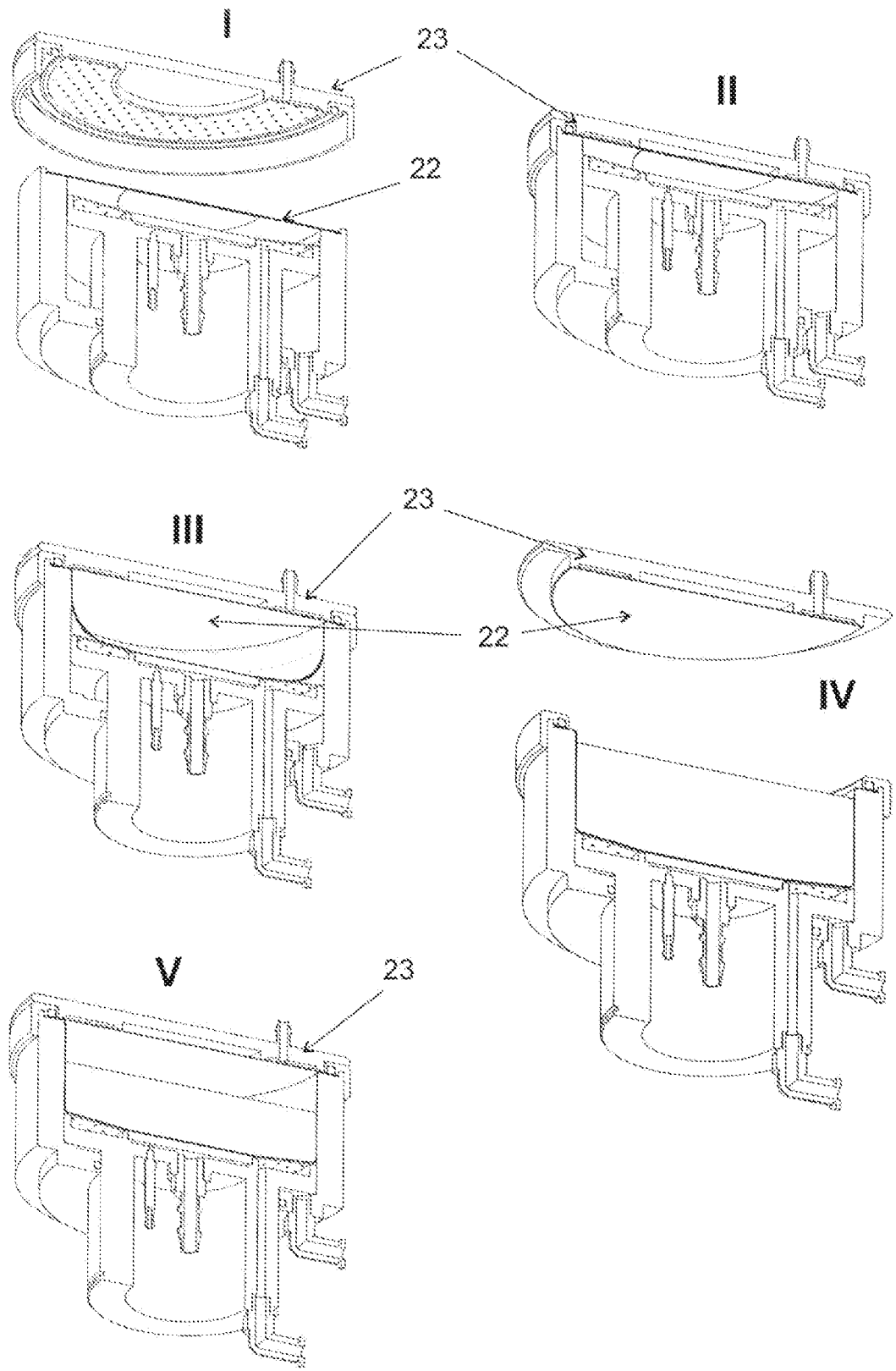
Figure 19:
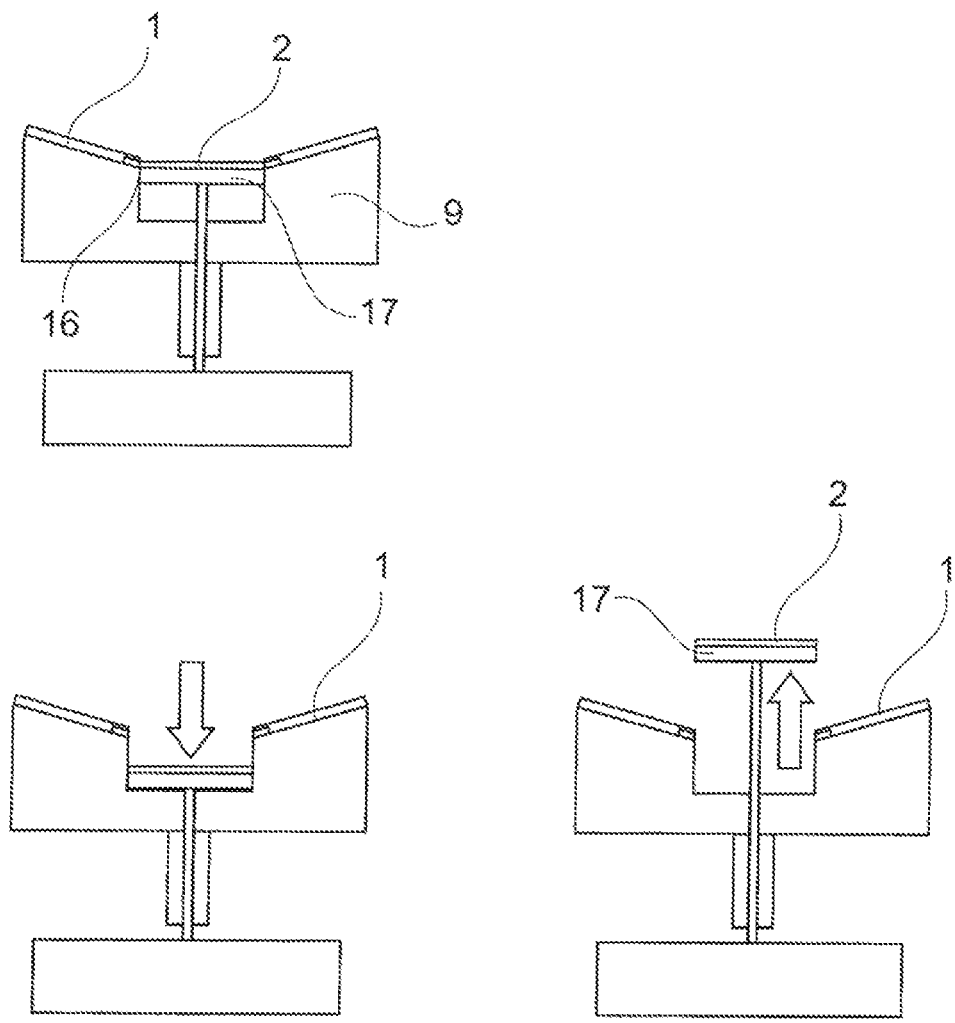
Figure 20:
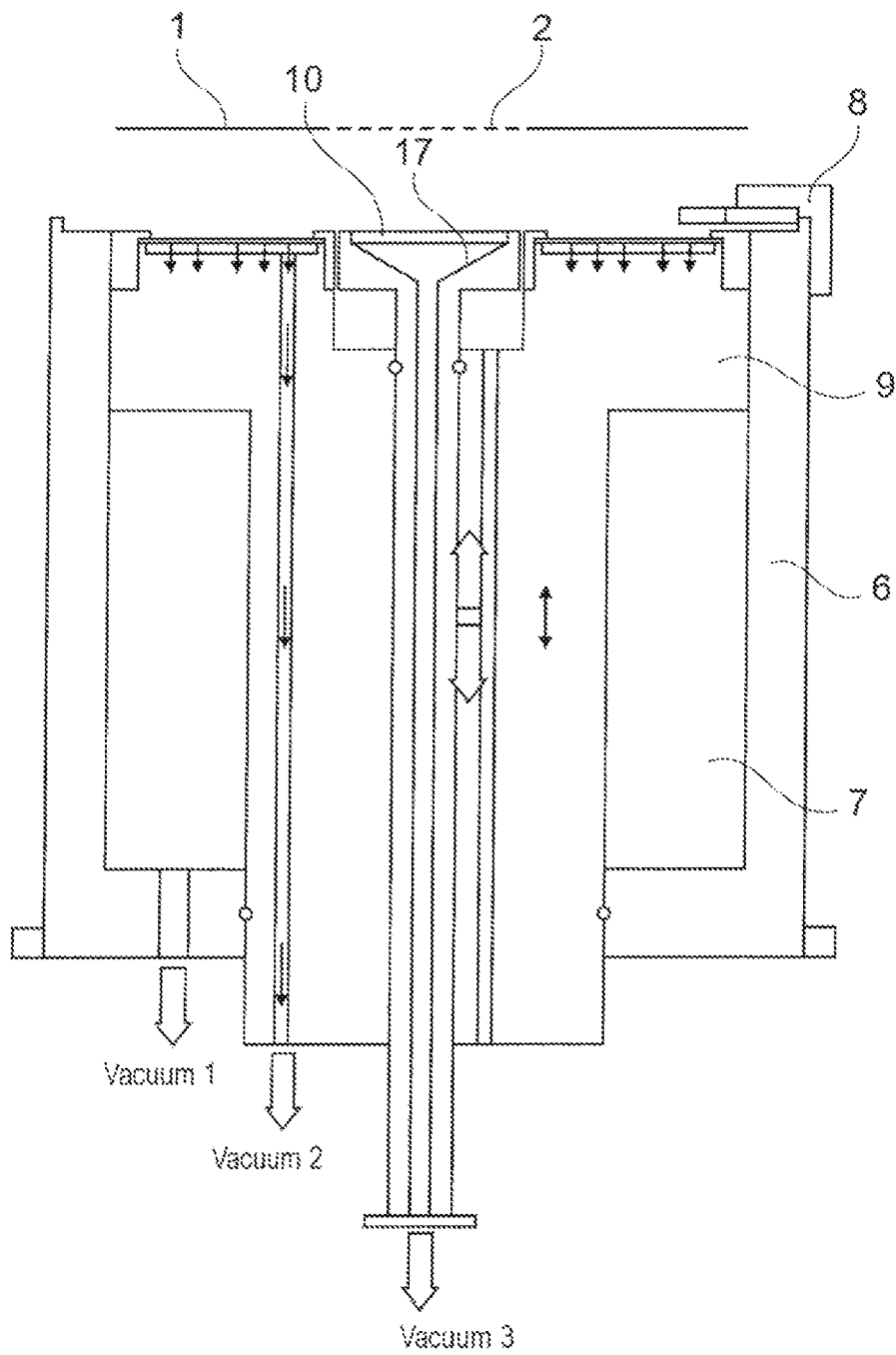

In the drawing:
FIGS. 1a and b show a blank of sheet material for use in the method and in combination with the apparatus of the present invention in two different embodiments;
FIG. 2 shows an example of a progressive deformation of a blank to form a funnel in accordance with the method and apparatus of the present invention;
FIGS. 3a, b and c show variations of the blank and membrane for use in the method and in combination with the apparatus of the present invention;
FIG. 4a shows an embodiment of an apparatus of the present invention in a partly cutaway view before the blank is placed on the holder;
FIG. 4b shows an embodiment of an apparatus of the present invention in a partly cutaway view shortly after the deformation process has commenced;
FIGS. 5a and 5b show the apparatus in a partly cutaway view in a further deformed state of the blank in two variations;
FIG. 6 shows a completely deformed state of the blank to explain specific aspects of the apparatus of the invention in a partly cutaway view;
FIG. 7 shows a completely deformed state of the blank during a filtration step in the apparatus of the present invention in a partly cutaway view;
FIGS. 8 and 9 show the step of removing the blank having formed the funnel in the apparatus of the present invention in a partly cutaway view;
FIG. 10 shows a detail for facilitating the removal of the membrane of an embodiment of the apparatus of the invention in a partly cutaway view;
FIG. 11 shows the apparatus in a state where the membrane is fully accessible for manual removal;
FIG. 12 shows a schematic representation of the apparatus in a partly cutaway view in two different positions for creating different funnel volumes;
FIG. 13 shows a modification of the blank of the invention with tabs for handling;
FIG. 14 shows three different packaging formats for the blank of the invention;
FIGS. 15 and 16 show a modification of the blank including a protective film;
FIGS. 17 and 18 show a modification of the apparatus including a cover mechanism for temporarily removing the protective film;
FIG. 19 shows a further modification of the apparatus including a means for separating the filtration medium from the blank; and
FIG. 20 shows the apparatus of FIG. 19 in cross section.

DETAILED DESCRIPTION OF PREFERRED EMBODIMENTS

The method and apparatus of the invention for filtering a liquid sample are based on the general concept of providing a blank of a deformable sheet material and a filtration medium and applying a force to deform and expand at least a portion of the blank at the point and time of filtration to form a funnel extending above and about the filtration medium. This funnel may hold the liquid sample introduced into it and allows filtering of the liquid sample from the funnel through the filtration medium into a downstream receptacle or drain.

The filtering through the membrane may be assisted by the application of pressure from the side of the funnel or the upstream side with respect to the filtration medium and/or of vacuum to the downstream or drain side of the filtration medium.

After the filtration is completed the force applied to deform and expand the blank to form the funnel is released and the funnel may completely or at least partially return to its initial sheet configuration.

The blank of the material is then separated and removed from the filtration medium and is discarded.

Figure 1B:
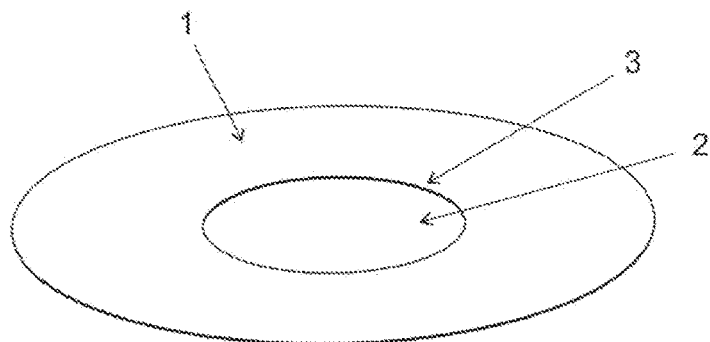

A suitable blank of sheet material for use in the method and in the apparatus (to be described later) of the present invention is shown in FIGS. 1a and 1b. The blank 1 is made from a sheet-like material that is liquid impermeable and has, preferably in a central area, an opening portion 1d for passing a liquid. The opening portion may be a central round cut-out as shown in the FIG. 1a but may also be formed by a cut-out of different shape or by a plurality of openings or perforations. The blank is made from a material that has elasticity and/or plasticity/ductility and the material is selected depending on the expansion and elongation performance required. Suitable materials are latex, paraffin, poly olefin, TEFLON® (polytetrafluoroethylene), thermoplastic elastomer, polyurethane, polyurethane, polypropylene, polyethylene, silicon, PVDF, certain papers or combinations thereof. A material referred to as "PARAFILM®" is a particularly preferred material for forming the blank. PARAFILM® is a plastic paraffin film with a paper backing produced by Pechiney Plastic Packaging Company, Chicago, U.S.A. primarily used in laboratories. It is commonly used for sealing or protecting vessels. It is ductile, malleable, waterproof, odorless, thermoplastic, semi-transparent and cohesive. Thermoplastic polyurethane such as PLATILON® from BAYER® MaterialScience AG, Germany, is also a preferred solution with a very high elasticity, weldability and water proof barrier.

Other suitable materials comprise "DURASEAL®" (a polyethylene-based film, available from Diversified Biotech, Dedham, Mass., USA) films. The dimensions and shape and thickness of the blank material are selected according to the deformation performance of the material and the desired expansion which determines the volume of the final funnel that can be achieved by deforming the blank before the material breaks or tears. The target volume of the funnel is preferably a range from 50 ml to 250 ml, preferably 100 ml or more, but larger volumes or smaller volumes are feasible. The blank is dimensioned such that deforming of it to the funnel creates the desired hold-up volume of the formed funnel, preferably of at least 100 ml, preferably of at least 200 ml.

A typical shape for the blank is disk-shaped or annular with the cut-out opening portion or the perforated opening portion located in the centre.

The blank is identified with the reference numeral 1 throughout the figures.

A filtration medium 2, preferably in the form of a membrane, is provided so as to cover the opening portion of the blank and the filtration medium is liquid tightly connected or connectable to the blank and is dimensioned such that it entirely covers the opening portion to avoid that liquid passes from the funnel, i.e. from an upstream side of the filtration medium to a downstream side of the filtration medium without passing through the medium.

Figure 3B:
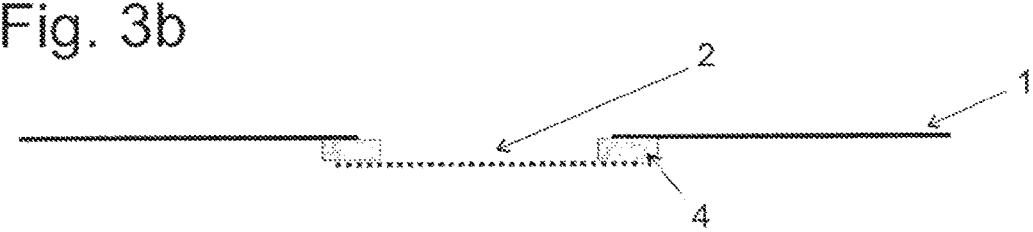

The filtration medium may be connected to the blank from the upper side or from the lower side as schematically shown in FIG. 3a and may, from either side, be connected to the blank via an intermediate piece 4 which can be a film or a adhesive that is placed between the medium and the blank. Such intermediate piece 4 is schematically shown in FIG. 3b and may serve the purpose to create a temporary or permanent seal and/or to protect or stiffen the medium during the forming of the funnel and/or during the handling subsequent to the filtration. The filtration medium may accordingly be permanently or releasably welded or adhered to the blank as shown in FIG. 1b through a seal/weld 3 or may simply be placed on the material forming the blank directly or with an intermediate piece provided a liquid tight sealing interface can be formed. The forming of the sealing interface without welding or adhesive, at least during the step of forming the funnel by deforming the blank can be assisted, as described later, by vacuum force applied to the blank and/or the medium.

Figure 3C:
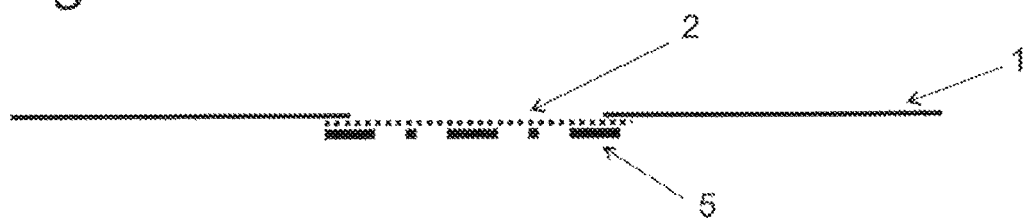

In a further embodiment that is schematically shown in FIG. 3c an underneath piece 5 in the form of a porous film or adhesive can be placed underneath the membrane to be used, for example as an aseptic separator. The connection between the underneath piece 5 and the membrane 2 may create a temporary or a permanent seal. The underneath piece could be made of soluble materials.

The underneath piece 5 may also represent a grid or supporting element for the forming process, the filtration, and/or the subsequent handling of the membrane after filtration if the filtration material is particularly delicate or frangible and not sufficiently self-supporting.

The filtration medium is selected according to the purpose, i.e. dependent on the particles or micro organisms to be collected and is, except for the dimensions and its interface with the blank described above, not specifically designed for the method and apparatus of the invention. Therefore, any suitable material known in the art can be used in principle.

The FIG. 2 shows three stages of the progressive deforming and extension of the blank 1 wherein 1a identifies a peripheral portion of the blank, 1b identifies an intermediate portion that will form a peripheral wall portion of the funnel and 1c represents a more central portion that will form a bottom portion of the funnel. The entire funnel accordingly surrounds the filtration medium 2 at the more central portion 1c of the blank representing the opening portion (either by a central hole or a perforated area), wherein the shape of the funnel can be pot-like as shown in FIG. 2 or may be formed with more conical peripheral walls. The diameter and the depth of the funnel are chosen to achieve the desired volume for the liquid sample. As described above, this can be achieved by selecting the shape and the dimensions of the blank that will produce the desired volume and shape of the funnel when the pulling and expanding force is applied to deform the blank of sheet material.

The main component parts of an apparatus for filtering a liquid sample in accordance with the present invention employing the method of the invention are schematically shown in FIGS. 4 to 12 in cross section and in the various stages of the operation wherein detail that are not necessary to explain the invention are omitted.

The apparatus comprises a bowl 6 defining an internal cavity 7 which defines the size and possibly the shape of the funnel to be formed from the blank 1 of material. A first holder 8 for holding a peripheral portion 1a of the blank of material cooperates with the bowl 6 (see FIG. 7) and a piston 9 is located in the cavity 7 so as to be movable relative to the bowl in the cavity. The piston 9 includes a support 10 for the filtration medium 2, most preferably a membrane, which is located at a central portion of the piston and the support 10 communicates with a drain for the liquid be filtered through the filtration medium. The piston 9 also comprises a holder 11 for holding the more central portion 1c of the blank of sheet material 1 about the support 10 for the filtration medium. This second holder 11 is preferably formed as a sieve with a number of perforations or grooves formed in large density which is further formed in a flat or slightly conical surface (see FIG. 6). A vacuum source 13 is connected or is removably connectable via a port to one or more channels in the piston 9 communicating with the second holder 11 for creating a sub-ambient pressure at the second holder that applies an attracting and holding force to the more central portion 1c of the blank when vacuum is applied.

The second holder in the peripheral vicinity of the filtration medium is preferably formed such that no elongation of the blank and of the medium occurs so as to avoid separation of the liquid tight sealing state between the blank and the filtration medium that is formed either by welding or adhering or simply by a pressure contact between the filtration medium (and possibly an intermediate piece as shown in FIG. 3b) and the blank material.

The support 10 for the filtration medium communicates with the drain and, preferably, with a vacuum source 12 for assisting the filtration. The support fully supports the medium 2 and is formed from a highly porous material (i.e.

a stainless steel mesh or a polymer frit) so that the sample liquid can be drained through the medium either when pressure is applied on the upstream side of the medium and/or when vacuum is applied from the downstream or drain side of the medium. The draining vacuum is applied preferably when a predetermined volume of the sample liquid has been filled in the funnel to avoid an early start of the filtration.

The relative movement of the piston and the bowl that effects the deformation and expansion of the blank to the funnel can be effected by way of a further vacuum source 14 communicating with a chamber 26 formed between the piston and the bottom of the bowl as shown in FIG. 4b. By applying the vacuum to the chamber 26 the piston 9 is moved towards the bottom of the bowl 6 and the movement can be reversed by applying pressure to the chamber 26 through the communication channel.

In the shown arrangement of the apparatus of the invention the bowl is stationary and the piston is moved. A reversal of this arrangement is possible, i.e. the piston may be fixed and the bowl may be alternatively moved relative to it. A simultaneous movement of both, i.e. of the bowl and of the piston is also possible. While a hydraulic drive of the piston relative to the bowl is shown and described, a mechanical drive arrangement including a motor and gears or a direct linear electric drive is possible but is not shown in the drawings.

While the cavity 7 of the bowl 6 shown in the drawing substantially corresponds to the shape of the funnel to be formed from the blank of material by deforming it when the piston is moved relative to the bowl, this volume does not necessarily have to be circular and its profile in cross section not necessarily has to correspond to the desired profile of the funnel. As shown in FIG. 5a certain parts of the blank may be freely stretched between the first holder 8 and the second holder 11 so as to either assume a radius or a conical shape. Alternatively, as shown in FIG. 5b, the second holder 11 may extend nearly to the outer periphery of the piston and in this case the funnel will assume a substantially pot-shape since the entire bottom portion of the blank can be held adhered to the top surface of the second holder of the piston. In a further modification the bowl could be reduced to the function of the first holder and the cavity could be simply a space below the first holder if the driving of the piston is effected by a mechanism that does not require the sealing engagement between the cavity of the bowl and the piston as in the hydraulic drive described above. For example, the hydraulic driving mechanism could include a separate cylinder/piston arrangement located so as to effect the desired reversible relative movement between the bowl/first holder and the piston/second holder.

As mentioned above, the volume of the cavity determines the volume of the funnel to be formed from the blank. There may, however, be distinct intermediate positions of the relative motion between the piston and the bowl creating funnels of different volume as shown for example in FIG. 12. This means, that, based on the same or different blank, different volumes of funnels can be created with the same apparatus simply in that the piston (or the bowl) is moved only a fraction of the possible relative stroke. In order to define such intermediate volumes, adjustable stop positions can be provided or a grading 27 can be provided to the bowl so as to indicate to user the current volume of a funnel.

As explained above, the liquid tight connection between the blank and the membrane can be permanent or semi-permanent (by welding or adhesive) or can be temporary only as long as the filtration medium is pressed against the blank material during the forming process, thereby forming a temporary seal as long as the vacuum force is applied to the more central section 1c of the blank and/or the medium.

The operation of the apparatus shown in the drawing for filtering a liquid sample is as follows:

First, the blank 1 of deformable material sheet is placed on a support surface of the bowl 6 and is held at its peripheral portion 1a by means of the first holder 8. At this time, the piston 9 is located at its upper position where its top surface is substantially flush or substantially continuous with the support surface for the peripheral portion 1a of the blank. Such a position is shown in FIG. 4a.

After the blank is fixed by means of the first holder, the second holder 11 for holding the more central portion 1c of the blank about the support 10 for the filtration medium is activated to fix this portion, and then the piston is moved downward. This starts the deformation and expansion process while the first and second holders maintain their holding force on the peripheral portion 1a of the blank and on the more central portion 1c of the blank 1, respectively. Such a position is shown in FIG. 4b.

An intermediate position between the starting position and the final position is shown, for example, in FIGS. 5a and 5b. Once the piston has reached the stroke corresponding to the desired degree of deformation of the blank or volume of the funnel formed by its deformation, the piston movement is stopped while the first and second holder still maintain their holding force on the blank (see FIG. 6). Then, as shown in FIG. 7, the liquid sample is filled into the funnel and the draining of the liquid sample through the filtration medium on the support is started, preferably by applying a vacuum on the downstream or drain side of the medium.

Once the entire sample liquid has been pulled from the funnel through the filtration medium to the drain, the piston is moved back to its initial position and the temporary deformation and expansion of the blank is released and more or less reversed. During this reverse movement of the piston the vacuum force applied on the support for the filtration medium is preferably maintained so as to retain the filtration medium in position. Once the piston has reached its home or starting position, the holding force applied by the first and second holders is released and the blank of material is removed from the apparatus (see FIG. 9). The removal of the blank can be assisted in that the vacuum force applied by the second holder 11 not only is released but in that a light back pressure is applied through the communication channels and the openings/grooves in the sieve (see FIG. 8). The first holder 8 is only schematically shown in FIGS. 8 and 12 and is omitted in the other figures for clarity purposes.

Finally, the filtration medium 2 is removed from the support 10 in that the vacuum applied from the side of the drain is released so that the membrane can be removed with tweezers (see FIG. 11). Preferably, additional means for assisting separation of the filtration medium from the blank and/or the support can be provided in the form of a rod-shaped actuator 15 shown in FIG. 10 for lifting the support or the medium, by applying a light hydraulic back pressure through the drain channel. The actuator 15 may be mechanically or hydraulically activated or may be automatically moved during the upward movement of the piston by way of a mechanical linkage or a mechanical force applied by a biasing means like a spring or the like that is released at one point during the upward movement.

In order to release the filtration medium from the support, the support can be lifted up completely providing access to an edge of the medium, or the medium only can be lifted up by means of the actuator facilitating gripping of an edge portion of the medium.

If the filtration medium is welded or otherwise permanently connected to the blank of material, a cutting device 16 may be provided so as to cut the filtration medium just after the filtration step (see FIGS. 19 and 20). For this purpose, a movable die 17 may be provided to cut and lift the medium from the piston 9 after cutting. In this case, the medium may be removed from the die 17 by means of tweezers and the blank of material may be retained in the cavity of the bowl for subsequent removal. The movable die 17 in this case can be formed as an element that includes cutting instruments for separating the medium from the blank but the cutting tool can be provided separately. The operation of the die for cutting and/or lifting the membrane can be also either hydraulically or mechanically actuated. A hydraulically activated version is shown in detail in FIG. 20.

FIG. 13 discloses a preferred embodiment of the blank which is provided with one or more peripheral tabs 27 which facilitate the handling during the loading and the unloading operation into and from the apparatus in that the contact with the sterilized blank and membrane can be more securely avoided. Furthermore, the peripheral tabs can be formed so as to interact and engage with the first holder for holding the peripheral portion of the blank within the apparatus during the deformation step.

FIG. 14 shows various packaging formats for the blank with or without the filtration membrane, which packaging formats can comprise individual pouches 18, a leporello or accordion-style folded package in the form of a band with sequentially arranged individual pouches 19, or a rolled tape provided in a dispenser 20, wherein the connection between the individual pouches on the tape may be pre-cut or incised in addition to the folding so that the individual pouches are releasably provided. Alternatively the blanks can be releasably provided on a supporting strip 21. Other packaging formats are possible as long as the requirements of a sterile transport and handling are fulfilled.

The blanks can be either packaged together with the membrane permanently or semi-permanently held in place on the opening portion of the blanks as described above or the membranes can be packaged separately from the blanks.

Additional aspects of the present invention will now be described.

In order to avoid external contamination of the filtration medium and the blank of deformable material sheet a protective film or foil 22 may be provided in that it is, for example, welded or sealed to the blank 1 at the peripheral diameter 1*a*, thereby covering the upper portion of the blank and of the filtration medium that will, after deformation and expansion, form the funnel for receiving the liquid sample. A part of the foil within the peripheral boundaries can be pre-cut or penetrated by appropriate tooling, for example once the blank with the foil is placed in the apparatus and held by the first holder, so as to allow the deformation of the blank to form the funnel (by providing entry of atmospheric pressure or an inert gas into the volume of the funnel) and allowing filling of the liquid sample into the volume of the funnel. If the foil remains connected with the peripheral diameter of the blank, it can provide some additional rigidity or support for the blank during the loading and unloading steps. Such a structure is shown in FIGS. 15 and 16.

In order to allow a temporary opening and closing of the protective film 22, the apparatus may be provided with a cover mechanism which comprises a removable cover 23 (see FIG. 17) which is provided, at an underside, with a perforated grid or openings 24 in communication with a further vacuum source allowing attraction of the protective film 22 to the underside of the removable cover 23 which could be either the protective film described above or a separate protective element. The sequence of steps for temporarily removing the protective film 22 from the blank being deformed to form the funnel by means of the cover mechanism including the vacuum source for allowing filling of the liquid sample is shown in FIG. 18. In this figure, the first step I is to place the cover 23 on the edge of the bowl, preferably providing a hermetical seal with the protective film 22, step II shows grabbing of the protective film 22 by means of the vacuum. Lifting up of the cover 23 together with the protective film 22 is shown in step III. The final step IV then shows how the protective film 22 is put back onto the blank so as to close the internal volume of the funnel.

While the present invention has been described above using a blank of a temporarily deformable material as an example, the remaining deformation of the blank after removal from the apparatus depends on the inherent properties of the material. If the material has a certain plasticity/ductility, it will retain at least a part of its deformed funnel shape. This is acceptable as it facilitates removal of the blank from the apparatus and is moreover not problematic as the blank is normally discarded after the use. While the above described apparatus uses hydraulic activation for effecting the various movements of pistons and/or bowls and/or other devices, a mechanical drive means is alternatively possible for each individual moving task. Even direct drive by means of a servo motor is feasible.

The described examples are based on an annular/round shape of the blank that is transformed to the funnel. It is a matter of course that other shapes of the blank, i.e. square or rectangular or elliptic or star-shaped blanks are equally possible.

Finally, while the invention has been described using a disposable blank as an example, it is well possible within the concept of the present invention to re-use the blank for repeated filtration processes and, if required, to sterilize or clean the blanks after each use.

The invention claimed is:

1. An apparatus for filtering a liquid sample, comprising:
a bowl defining a cavity;
a separate blank of deformable sheet material having a peripheral portion and a central portion having an opening;
a filtration medium entirely covering said opening in said central portion of said separate blank of deformable material;
a first holder cooperating with said bowl to hold said peripheral portion of said separate blank of deformable sheet material on said bowl;
a support in said bowl for supporting said filtration medium; and
a piston movably mounted in said bowl, said piston comprising a second holder to hold said central portion of said separate blank of deformable sheet material, said second holder having a plurality of perforations extending therethrough for creating a sub-ambient pressure at the second holder for applying a hold down force to said central portion upon the application of vacuum by a source of vacuum to said second holder; said piston being movable relative to said bowl between a first position in said bowl and a second position in said bowl, wherein when said piston is in said first position, said separate blank of deformable material has a first hold-up volume, and when said piston is in said second position, said separate blank of deformable material has a second hold-up volume, said second-hold up volume being greater than said first hold-up volume, wherein said first hold-up volume and said second hold-up volume are contained by said separate blank of deformable sheet material as a result of moving piston downwards and deforming said separate blank of deformable sheet material.

2. The apparatus according to claim 1, wherein the cavity of the bowl has an inlet opening and an outlet opening spaced from said inlet opening, and wherein said inlet opening has a larger diameter than said outlet opening.

3. The apparatus according to claim 1, wherein the support is movable relative to the piston.

4. The apparatus according to claim 1, further comprising an actuator for separating the filtration medium from the separate blank of deformable sheet material.

5. The apparatus according to claim 1, further comprising a protective film placed on the separate blank of deformable sheet material.

6. The apparatus of claim 1 wherein the filtration medium is a filtration membrane that is connectable to the separate blank of deformable sheet material in a liquid tight manner.

7. The apparatus of claim 1, wherein said second hold-up volume is at least 100 ml.

8. The apparatus of claim 1, wherein said second-hold-up volume is at least 200 ml.

9. The apparatus of claim 1, wherein said piston comprises a first channel in fluid communication with said plurality of perforations of said second holder.

10. The apparatus of claim 1, wherein said bowl has an inner peripheral wall, and said piston has an outer peripheral wall, and wherein there is a second channel between said inner peripheral wall of said bowl and said outer peripheral wall of said piston, said second channel being in fluid communication with said source of vacuum.

11. The apparatus of claim 10, wherein a portion of said outer peripheral wall of said piston abuts said inner peripheral wall of said bowl in sliding engagement.

12. The apparatus of claim 1, further comprising a first port in fluid communication with said vacuum source and said support, wherein application of vacuum through said first port assists filtration through the filtration medium on the support;

a second port in fluid communication with said vacuum source and said second holder; and a third port in fluid communication with said vacuum source and the apparatus, wherein the application of vacuum through said third port moves said piston relative to said bowl between said first and second positions.

* * * * *

UNITED STATES PATENT AND TRADEMARK OFFICE
CERTIFICATE OF CORRECTION

| | |
|---|---|
| PATENT NO. | : 10,549,218 B2 |
| APPLICATION NO. | : 14/119496 |
| DATED | : February 4, 2020 |
| INVENTOR(S) | : Olivier et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 447 days.

Signed and Sealed this
Twenty-fourth Day of November, 2020

Andrei Iancu
*Director of the United States Patent and Trademark Office*